United States Patent [19]

Makiuchi et al.

[11] Patent Number: 5,047,351
[45] Date of Patent: Sep. 10, 1991

[54] OPTICAL END-POINT TYPE ANALYTICAL METHOD

[75] Inventors: Hajime Makiuchi; Yuzo Iwata; Kikuo Hirai; Kenji Murabayashi, all of Saitama, Japan

[73] Assignee: Fuji Photo Film Co., Ltd., Kanagawa, Japan

[21] Appl. No.: 351,315

[22] Filed: May 10, 1989

Related U.S. Application Data

[63] Continuation of Ser. No. 91,985, Sep. 1, 1987, abandoned.

[30] Foreign Application Priority Data

Sep. 1, 1986 [JP] Japan ................ 61-205604

[51] Int. Cl.$^5$ .................................. G01N 21/78
[52] U.S. Cl. .................... 436/169; 364/497; 422/56; 436/164; 436/172
[58] Field of Search .............. 436/34, 164, 169, 170, 436/172; 422/56; 364/497

[56] References Cited

U.S. PATENT DOCUMENTS 3,989,383 11/1976 Paulson ........................ 436/34
4,052,161 10/1977 Atwood et al. ............... 436/34
4,063,817 12/1977 Shimamura et al. ........... 436/34
4,399,225 8/1983 Hansen et al. ................. 436/34

Primary Examiner—Robert J. Hill, Jr.
Attorney, Agent, or Firm—McAulay Fisher Nissen Goldberg & Kiel

[57] ABSTRACT

A method for shortening the analysis time, without adversely affecting the accuracy in the colorimetric analysis of an analyte. The method including the steps of:

(a) Measuring the optical density for two or more times at suitable time intervals after the beginning of reaction to follow the variation of optical density,
(b) Judging based upon the optical density obtained at the earlier measurement whether the reaction is to be further continued or not,
(c) When it is judged that the continuation of the reaction is not necessary in terms of analytical accuracy, selecting the calibration curve corresponding to the reaction time,
(d) While, when it is judged that the continuation of the reaction is necessary, further continuing the reaction, and
(e) Repeating steps (b) and (d) until the judgement that the continuation of the reaction is not necessary is obtained.

2 Claims, 5 Drawing Sheets

OPTICAL END-POINT TYPE ANALYTICAL METHOD

This is a continuation of application Ser. No. 07/091,985, filed Sept. 1, 1987, now abandoned.

BACKGROUND OF THE INVENTION

1. Field of the Invention

This invention relates to an analytical method for determining a particular component in a fluid sample based on optical change, such as, colorimetry. More particularly, this invention relates to a method for shortening of analysis time in such an analytical method.

2. Description of the Prior Art

Colorimetric analysis is a method based on optical change, such as, coloring or color change, caused by the reaction of a suitable reagent with the object substance to be detected (analyte). In a conventional analysis using a chemical reaction in solution, a reagent which reacts with the analyte to produce an optical change is added to the sample solution. On the other hand, in the dry method recently developed, the liquid sample is spotted on an analytical element containing the reagent, and the optical change occurring in the element is measured. Examples of dry-type analytical elements are disclosed in U.S. Pat. No. 3,992,158, U.S. Pat. No. 4,292,272, etc.

As described above, when a reagent is added to a sample solution, or when a sample solution is spotted on a dry-type analytical element, the analyte in the sample reacts with the reagent to produce coloring or the like. For example, when a blood sample or a blood plasma sample is spotted on the dry-type analytical element described in U.S. Pat. No. 4,292,272, glucose in the sample reacts with the reagent to form a colored substance, such as, a red colored substance. The optical density of the dry-type analytical element corresponds to the amount of the colored substance produced. Therefore, the reflection optical density is measured after a prescribed time, and it is converted to glucose concentration (blood sugar value) by using a calibration curve obtained previously. In the wet method, transparent optical density is usually measured.

In the prior art, measurement of optical density has been measured only once after a prescribed time from the spotting of a sample solution or the addition of the reagent, except for a rate assay for determining enzyme activity or the like. However, in the case of a lower analyte concentration, the reaction finishes in a relatively short period, and it is generally not necessary to wait till the above prescribed time. On the other hand, for higher analyte concentrations, the analytical accuracy is lowered if the reaction time is short, because the slope of the calibration curve is small for such a case and thus the variation coefficient of the determined concentration increases.

SUMMARY OF THE INVENTION

An object of the invention is to provide a method capable of shortening the reaction time to the minimum without reducing the analytical accuracy in colorimetry.

Such an object can be achieved by the method comprising the steps of:

(a) Measuring the optical density two or more times at suitable time intervals after the beginning of reaction to follow the variation of optical density, (b) Determining based upon the optical density obtained at the earlier measurement, whether the reaction is continuing further, (c) If it is determined that the continuation of the reaction is not necessary in terms of analytical accuracy, selecting the calibration curve corresponding to the reaction time, (d) If it is determined that the continuation of the reaction is necessary, further continuing the reaction, and (e) Repeating said steps of (b) and (d) until it is determined that the continuation of the reaction is not necessary.

DETAILED DESCRIPTION OF THE INVENTION

Figure 1:
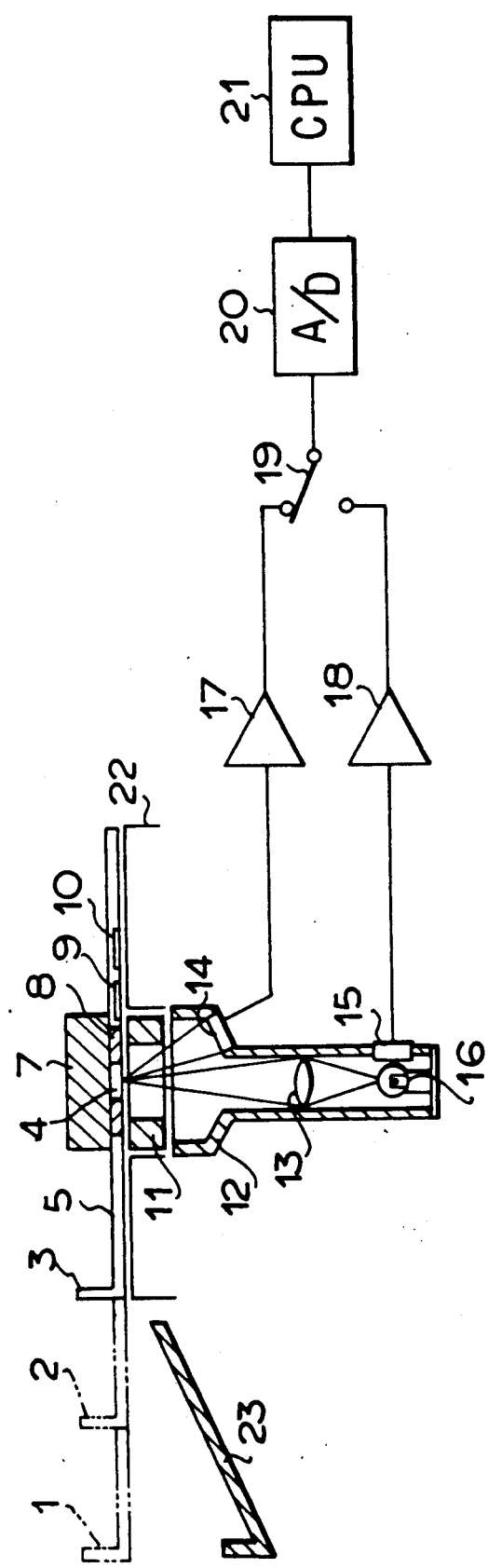
FIG. 1 is a sectional view of the analyzer employed in the example of the invention.

In the analytical method of the invention, the relationship between reaction time and optical density is first measured as to various analyte concentrations. The upper limit of the reaction time capable of obtaining the effective variation of optical density for each analyte concentration can be determined by the above relationships. Then, the boundary optical density as the index for the judgement whether the reaction should be continued or not is determined for each reaction time based upon the total increase or decrease of the optical density after that. Subsequently, the calibration curves for respective reaction times are obtained.

When a sample is analyzed by a dry method, the sample is spotted on an analytical element to initiate the color reaction. In the case of a wet method, a color reagent is added to the sample solution. The spotted or added time is approximately set as the time to initiate the color reaction. The analytical element or the reaction solution is kept under constant conditions. The measurements of optical density are preferably conducted at equal intervals of time. After the first prescribed time ($T_1$), the optical density of the analytical element or the reaction solution is measured. When the optical density does not reach the critical optical density ($TH_1$) at the first prescribed reaction time ($T_1$), the optical density at this time is converted to analyte concentration, by using the calibration curve for this reaction time. Then the analysis of next sample can be started. When the optical density is greater than the boundary optical density ($TH_1$), the reaction is further continued till the second prescribed time ($T_2$), and then the optical density is measured again. When the optical density does not reach the boundary optical density ($TH_2$) at the second prescribed reaction time ($T_2$), the optical density at this time ($T_2$) is converted to analyte concentration by using the calibration curve for this reaction time. Then, the analysis of next sample can be started. When the optical density is greater than the boundary optical density (TH$_2$), the reaction is further continued till the third prescribed time (T$_3$), and these steps are repeated (T$_4$, etc.). On the other hand, it is no longer necessary to repeat these steps after the variation of optical density obtained is sufficient to ensure analytical accuracy for the analyte concentration accurately. Therefore, a maximum reaction time should be predetermined for every analyte concentration by calibration experiments, prior to analyzing unknown samples.

The method of the invention is applicable to various colorimetries, and it is particularly effective in the colorimetries using various integral dry-type analytical elements because it is necessary that a large number of samples are measured efficiently. For example, this method is applicable to the colorimetries utilizing the following color reactions.

(1) Various color reactions detecting the hydrogen peroxide produced directly or indirectly by the reaction with analyte. For example, The coupling reaction between a phenazone, such as, 1-phenyl-2,3-dimethyl-4-aminopyrazoline-5-one or 1-(2,4,6-trichlorophenyl-2,3-dimethyl-4-aminopyrazoline-5-one and a phenol such as phenol, such as, phenol, α-naphthol or 1,7-dihydroxynaphthalene in the presence of peroxidase or other substances having peroxide catalyzing activity.

The color change reaction of a benzidine type chromogen, such as, benzidine, o-toluidine, o-dianisidine or tetramethylbenzidine in the presence of peroxidase, etc. (E.G. U.S. Pat. No. 2,981,606).

The color producing reaction from a leuco dye having an imidazole ring, such as, 2,4,5-triarylimidazole or 2,4-diaryl-5-alkylimidazole.

(2) The fomazan dye-forming reaction from a tetrazdium salt through an election transferring agent which conjugates with the oxidation reduction reaction between NAD and NADH or NADP and NADPH (e.g. Japanese Patent KOKAI No. 59-88097).

(3) The azobilirubin-producing reaction by bonding an aromatic diazonium salt and bilirubin (e.g. U.S. Pat. No. 2,854,317, U.S. Pat. No. 3,880,588, EP 0 115 873A, etc.)

(4) The azo dye-forming reaction by vanilmandelic acid and a diazonium salt, such as, p-nitrobenzene diazonium.

(5) The color-forming reaction from creatinine and a picrate (Jaffe's method).

(6) The color dissociation from a self coloring substrate in the presence of an enzymatic activity. For example, the hydrolysis producing p-nitrophenol from a p-nitrophenol-substituted oligosaccharide (U.S. Pat. No. 4,233,403), and the hydrolysis producing p-nitrophenol from γ-glutamyl-p-nitroanilide or p nitrophenol phosphate.

(7) The reaction of a naphthylamine such as N-(1-naphtyl)-N'-diethylethylenediamine with o-phthalaldehyde and urea in an acidic environment (e.g. Japanese Patent K0KAI Nos. 55-69038 and 58-117457).

(8) The chelate color-forming reaction between a metal ion, such as, calcium ion and a chelating reagent, such as, 3,3'-bis[{di(carboxymethyl)amino}methyl]-o-cresolphthalein.

(9) The color change of an acid-base indicator by pH. For example, the color changes of phenolsulfophthalein, Bromocresol Green and Bromocresol Purple.

(10) The color change of an acid-base indicator by protein. For example, the color changes of Bromocresol Green, Bromocresol Purple, Tetrabromophenol Blue and the like by albumin, utilizing for the analysis of ammonia or urea.

(11) The coloring of biuret reagent in an alkaline environment, utilized for the analysis of total protein.

The method of the invention is utilizable not only for color formation or color change but also for discoloration or decrease of colored material, such as the analysis of glucose by measuring the decrease of NADH or NADPH and the analysis of glucose by measuring the decrease of ferricianide.

The method of the invention is also utilizable for measuring the fluorescence emitted by the excitation using electromagnetic waves having short wave length, such as, ultraviolet rays or radioactive rays and for measuring the luminescence, such as, chemiluminescence and bioluminescence including the luminescence of luminol by the interaction of hydrogen peroxide.

By utilizing the method of the invention, the time for analysis can be shortened without reducing the accuracy in the determination of an analyte in a liquid sample, such as colorimetry. In the case of a conventional end-point method, only a single time is set for the reaction of samples containing the analyte in a wide range of concentration. Thus, the reaction time is excessive for the samples containing a lower concentration of the analyte. Since the method of the invention removes the waiting period for such excess of reaction time for lower analyte concentration, the total time for analysis is saved. This saving of time is particularly advantageous in the dry method of analysis in which the shortening of time required for the analysis is important.

On the other hand, a longer time is required for the reaction of analyte is higher concentration so as to obtain a sufficient accuracy of the analysis, because a shorter reaction time causes a lower slope of the calibration curve which leads to insufficient accuracy with a greater variation coefficient. Since such a tendency is prevailing in the dry method analysis, selection of the reaction time is important. A reasonable shortening of analysis time can be achieved by this invention without deterioration in the accuracy of analysis, not only due to the simple shortening of reaction time, but also based on the selection of a minimum reaction time depending on the concentration of analyte in the sample, so as to obtain sufficient accuracy.

EXAMPLE

Preparation of Chemical Analytical Slide

A dry type chemical analytical slide for the analysis of glucose was prepared as follows.

The support employed was a colorless transparent polyethylene terephthalate film having a thickness of 180 μm on which a gelatin under coating was provided. The following aqueous solution was applied on the support so that its dry thickness became 15 μm, and dried to form a reagent layer.

| | |
|---|---|
| Gelatin | 20 g |
| Peroxidase | 2,500 IU |
| Glucose oxidase | 1,000 IU |
| 1,7-Dihydroxynaphthalene | 0.5 g |
| 4-Aminoantipyrine | 0.5 g |
| Polyoxyethylene nonyl phenyl ether | 0.2 g |
| Water | 200 ml |

The following aqueous solution was applied thereon so that the dry thickness became 7 μm, and dried to form a light-blocking layer.

| | |
|---|---|
| Gelatin | 10 g |
| Titanium dioxide | 100 g |
| Water | 500 ml |

The following aqueous solution was applied on the light-blocking layer so that its dry thickness became 2 μm, and dried to form an adhesive layer.

The above adhesive layer was dampened with 30 g/m² of water, and a cotton broad woven fabric was lightly pressed on it to laminate it as a spreading layer, followed by drying.

The film for the analysis of glucose was cut into pieces having a size of 15×15 mm, and each piece was placed in a plastic mount of 24×28 mm to obtain an analytical slide.

Figure 2:
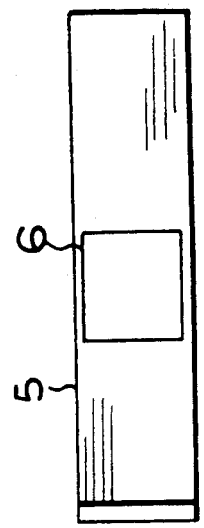
FIG. 2 is a plan view of the slide loading lever of the analyzer.
Figure 3:
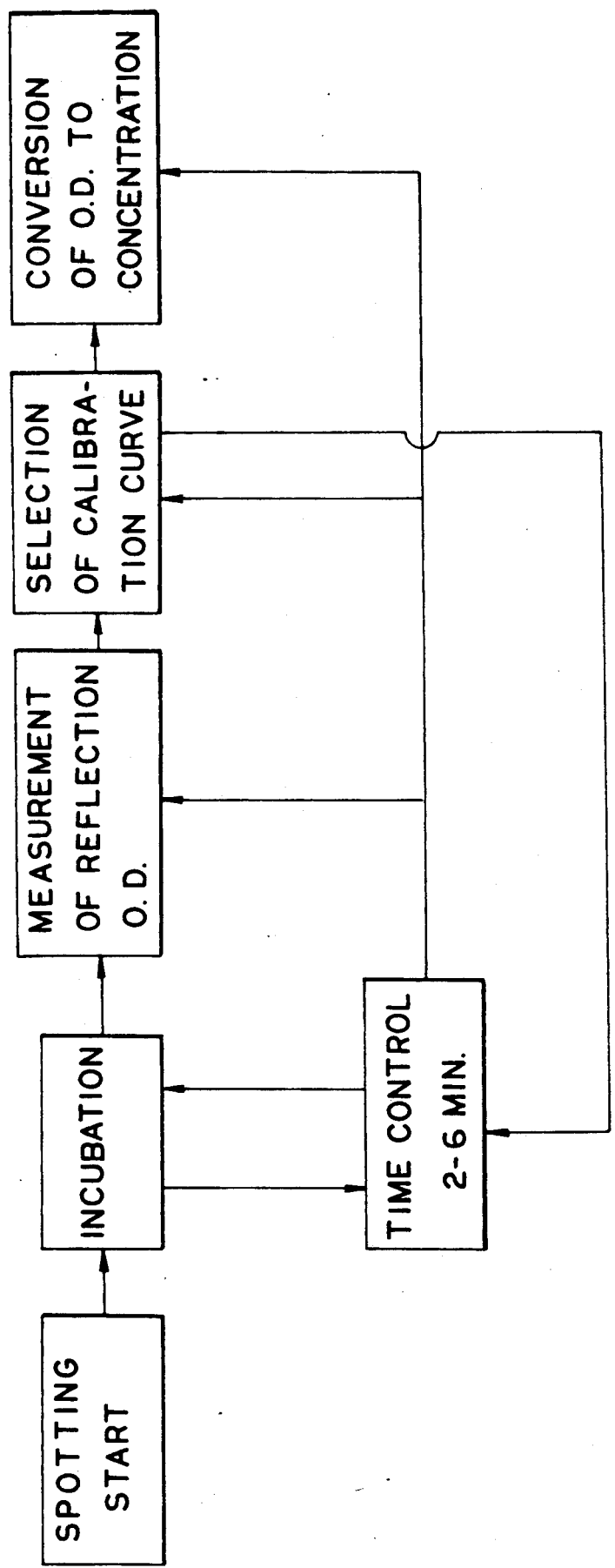
FIG. 3 is a representative flow diagram.

Determination of Boundary Optical Densities and Preparation of Calibration Curves at Each Reaction Time The analyzer shown in FIG. 1 was employed. The analytical slide 8 was loaded in the loading place 6 of a slide-loading lever 8 having the shape of FIG. 2 at the slide-loading position 2, and 10 μl of a sample solution was spotted on the film for the analysis of glucose 4 of the analytical slide 8 by using a micropripet. Immediately, the slide loading lever 5 was pushed into the photometric position 3, and thereby the analytical slide 8 was placed in an incubator 7 as shown in FIG. 1. The FIG. 9 indicates a black plate, and the FIG. 10 indicates a white plate. These are utilized for adjusting the colorimeter. The FIG. 11 indicates an auxiliary heater heating the analytical slide 8 from the underside. The analytical slide 8 was incubated, and the reflection optical density was measured from the side of the support of the film 4 automatically at one minute intervals by a timer provided in the analyzer. The light for measurement was emitted from a light source 16 disposed in a photometric head 12, and condensed by a lens 13 to the position of the analytical slide 8. The reflected light was received by a photometric part 14, and multiplied by an amplifier 17. On the other hand, the light for the reference was received by the other photometric part 15, and multiplied by the other amplifier 18. 19 is a switch, 20 is a A/D converter, and 21 is a computer. After the measurement, the analytical slide was taken out by pulling out the slide-loading lever 5 to the slide detaching position 1, and dropped into a slide discharging tray 23. 22 indicates a base plate.

Figure 5:
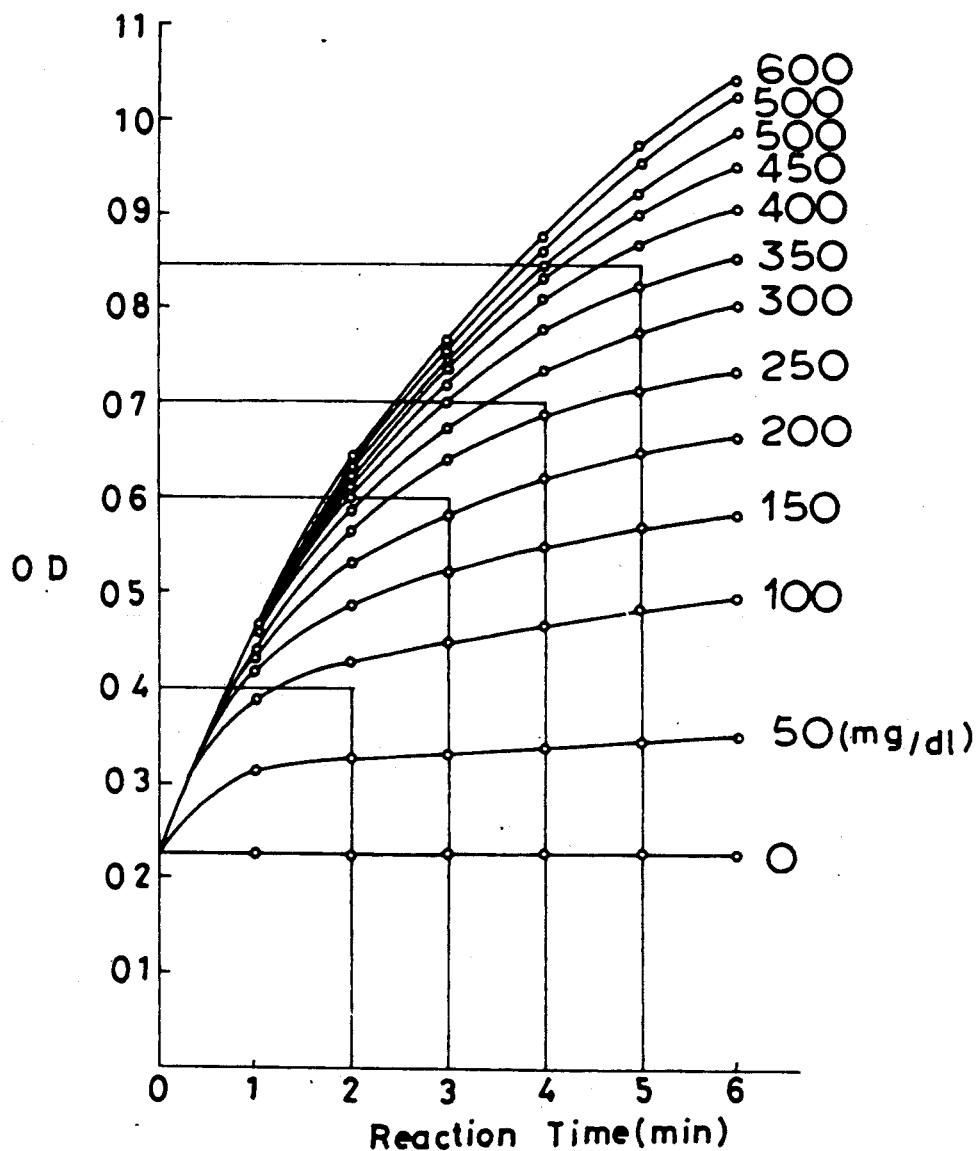
FIG. 5 is a graph indicating the relationships between the reaction time and the reflection optical density measured by using sera containing glucose in various concentrations.

Using this analyzer, and the foregoing analytical slide, the relationship between the reflection optical density and reaction time was measured as to the control serum containing glucose in concentrations of 0, 50, 100, 150, 200, 250, 300, 350, 400, 450, 500, 550, or 600 mg/dl (a commercial control serum and the samples thereof to which glucose of each concentration was added). The reflection optical density of each analytical slide was measured at one minute intervals untill six minutes after spotting of each control serum. The results are shown in FIG. 5. From these results, boundary optical densities were decided as 0.400 ($TH_1$) at 2 minutes, 0.600 ($TH_2$) at 3 minutes, 0.700 ($TH_3$) at 4 minutes and 0.850 ($TH_4$) at 5 minutes. The glucose concentrations of all the remaining samples passed through the threshold optical density at 5 minutes were measured at 6 minutes after the starting of the reaction.

Figure 6:
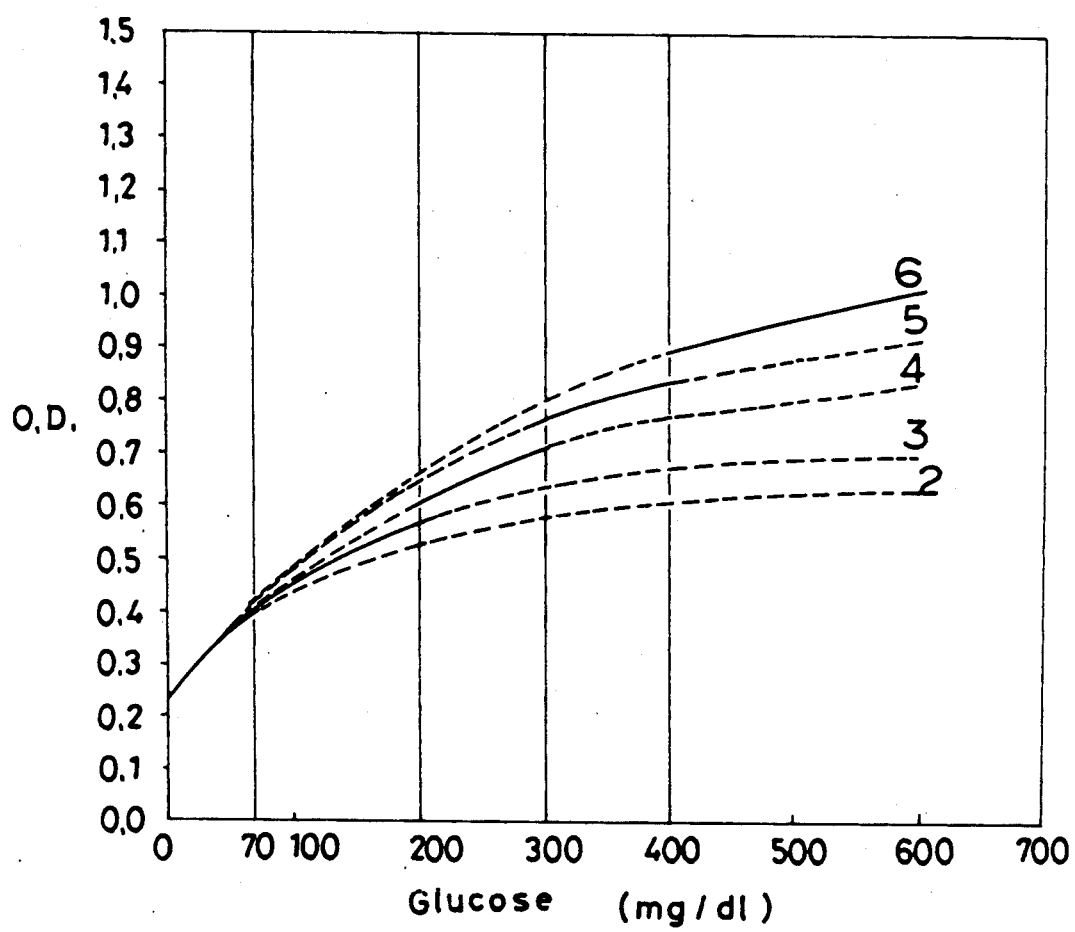
FIG. 6 is a graph indicating the calibration curves for each reaction time.

Subsequently, respective calibration curves 2, 3, 4, 5 and 6 minutes were measured, and are shown in FIG. 6.

Analytical Operation

Figure 4:
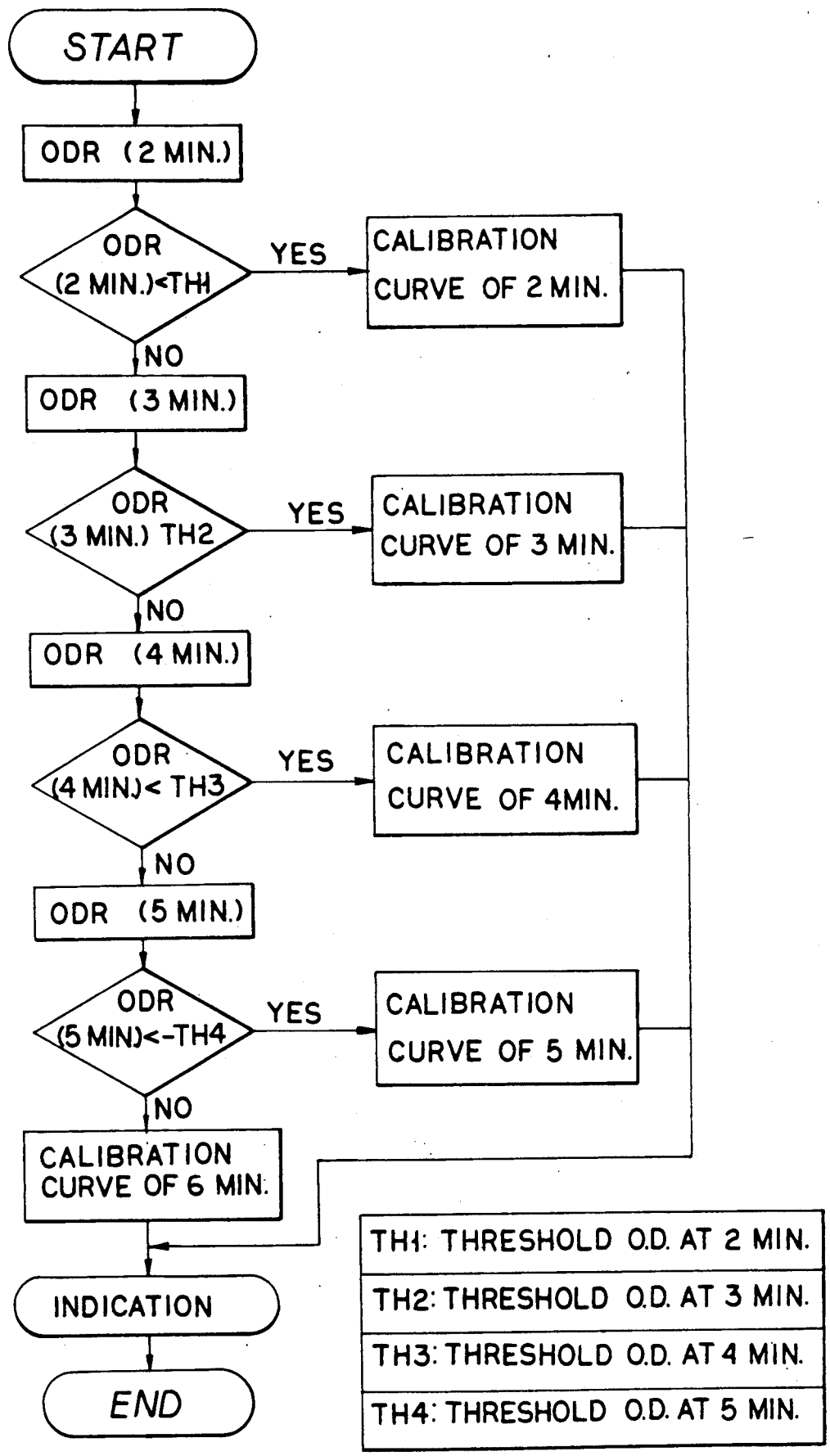
FIG. 4 is the logic diagram employed in the example.

The logic diagram employed in the example is shown in FIG. 4.

Each analytical slide is loaded in the slide-loading lever, and 10 μl of a sample solution is spotted. Immediately, the slide-loading lever is pushed into the photometric position, and thereby incubation is started.

The reflection optical density is automatically measured after 2 minutes ($T_1$) by the timer provided in the analyzer. When the reflection optical density is less than 0.400 ($TH_1$), glucose concentration of the sample is calculated from this optical density by using the calibration curve at 2 minutes after the starting of the reaction. The analytical slide is taken out of the incubator, and discharged into the tray. All calibration curves are memorized in the computer, and all calculations are carried out in the computer. While, when the reflection optical density is not less than 0.400 ($TH_1$), the reaction is further continued.

The reflection optical density is measured again after 3 ($T_2$) minutes from the spotting. When the reflection optical density is less than 0.600 ($TH_2$), the glucose concentration is calculated from this optical density by using the calibration curve at 3 minutes after the starting of the reaction. The analytical slide is taken out, and discharged into the tray. While, when the reflection optical density is not less than 0.600 ($TH_2$), the reaction is further continued.

After 4 minutes ($T_3$) and 5 minutes ($T_4$), similar operations are repeated.

After 6 minutes, the glucose concentration is calculated from the reflection optical density at 6 minutes after the starting of the reaction without judgement, and the analytical slide is discharged.

We claim:

1. A method of analyzing the concentration of an analyte using the end-point method and plural predetermined calibration curves showing the variation of the optical density or emission intensity with analyte concentrations at various predetermined time intervals by observing the variation in optical density or emission intensity of a sample occurring due to the reaction of the analyte, which comprises:

(a) measuring the optical density or emission intensity due to the reaction of the analyte at least once at a predetermined time interval after the beginning of the reaction;

(b) if the optical density or emission intensity obtained at the first measurement is smaller than a predetermined critical value ($TH_1$), selecting a predetermined calibration curve showing the variation of the optical density or emission intensity with analyte concentrations at various predetermined time intervals for a reaction time corresponding to said first measurement, and discontinuing the measurement, (c) if the optical density or emission intensity obtained at the first measurement is not smaller than a predetermined critical value ($TH_1$), continuing the reaction further until an optical density or emission intensity smaller than $TH_1$ wherein $l$ is at least 2 and $TH_1$ is greater than $TH_{1-1}$ for each time interval $T_1$ is obtained, then selecting a predetermined calibration curve showing the variation of optical density or emission intensity with analyte concentration at the predetermined time interval for a reaction time corresponding to the measurement where the optical density or emission intensity smaller than $TH_1$ is obtained for the first time, and discontinuing the measurement, and (d) determining the amount of the analyte using said selected calibration curve.

2. The method of claim 1 wherein the analysis is carried out using an integral dry-type analytical element.

* * * * *